United States Patent [19]

Grafen et al.

[11] Patent Number: 5,468,883
[45] Date of Patent: Nov. 21, 1995

[54] PREPARATION OF VITAMIN E

[75] Inventors: Paul Grafen, Weisenheim; Hans Kiefer, Neustadt; Hagen Jaedicke, Ludwigshafen, all of Germany

[73] Assignee: BASF Aktiengesellschaft, Ludwigshafen, Germany

[21] Appl. No.: 302,743

[22] PCT Filed: Mar. 5, 1993

[86] PCT No.: PCT/EP93/00498

§ 371 Date: Sep. 9, 1994

§ 102(e) Date: Sep. 9, 1994

[87] PCT Pub. No.: WO93/19057

PCT Pub. Date: Sep. 30, 1993

[30] Foreign Application Priority Data

Mar. 17, 1992 [DE] Germany .......................... 42 08 477.6

[51] Int. Cl.⁶ .................................................. C07D 311/72
[52] U.S. Cl. .................................................. 549/411; 549/410
[58] Field of Search ..................................... 549/411, 410

[56] References Cited

U.S. PATENT DOCUMENTS 3,459,773  8/1969  Moroe et al. .
3,708,505  1/1973  Greenbaum et al. .
4,217,285  8/1980  Yoshino et al. .

FOREIGN PATENT DOCUMENTS 2743920  3/1978  Germany .
2208795  9/1978  Germany .

OTHER PUBLICATIONS

Chem. Abstr., 84(1976) 59792X.

Chem. Abst. 73(1970) 77483z.

Chem. Abst. 84(1976)74471k.

*Primary Examiner*—Nicky Chan
*Attorney, Agent, or Firm*—Keil & Weinkauf

[57] ABSTRACT

A process for preparing dl-α-tocopherol or dl-α-tocopheryl acetate by acid-catalyzed reaction of 2,3,5-trimethylhydroquinone (TMH) with phytol or isophytol in a solvent at elevated temperature, with or without subsequent esterification of the resulting tocopherol with acetic anhydride, entails the reaction being carried out in the presence of a mixture of ortho-boric acid and certain aliphatic di- or tricarboxylic acids, preferably in the presence of a mixture of ortho-boric acid and oxalic acid.

4 Claims, No Drawings

PREPARATION OF VITAMIN E

This application is a 371 of PCT/EP93/00498 filed Mar. 5, 1993.

The present invention relates to an improved process for preparing vitamin E by acid-catalyzed reaction of 2,3,5-trimethylhydroquinone (TMH) with a phytol.

The preparation of dl-α-tocopherol (vitamin E) by reacting TMH and a phytol, for example isophytol (IP), at elevated temperature in a solvent of low polarity in the presence of various acid catalysts has been disclosed.

According to statements in Chem. Abstracts. (C.A.) 84 (1976) 59792 and C.A. 85 (1976) 46898, it is possible to carry out the reaction in the presence of $SiO_2/Al_2O_3$ with acids.

According to C.A. 73 (1970) 77483, C.A. 80 (1974) 3385, C.A. 80 (1974) 3386, C.A. 73 (1970) 98799 and DE-A 22 08 795, the reaction can also be carried out in the presence of $ZnCl_2$ together with acids such as hydrohalic acids, especially HCl, trichloroacetic acid or acetic acid.

According to the statements in DE-A 22 08 795 it is also possible to use $ZnCl_2$ mixed with $NaHSO_4$, sulfuric acid or p-toluenesulfonic acid in a molar ratio of from 1:3 to 1:1.

According to the statements in C.A. 84 (1976) 74471, the reaction can be carried out in the presence of a mixture of $SiO_2$ and $Al_2O_3$ in the ratio 87:13 as catalyst in perchloroethylene.

According to U.S. Pat. No. 3,459,773, vitamin E is obtained by reacting phytol or isophytol with TMH in an inert solvent using a macroreticular cation exchanger resin of the sulfonic acid type.

It is common to all these known processes that the vitamin E cannot be prepared in the required purity on the industrial scale.

To overcome this problem, the reaction disclosed in DE 27 43 920 is carried out in the presence of a mixture of silica and alumina or silica gel and zinc chloride and a strong acid such as concentrated HCl, $H_2SO_4$, $H_3PO_4$ or p-toluenesulfonic acid.

The disadvantages of this process are, as with many of the abovementioned processes, that problems with corrosion arise, and that the wastewater may be polluted with zinc ions.

It is an object of the present invention to find a catalyst system for reacting TMH and phytol or isophytol to give vitamin E which can be used to prepare vitamin E more advantageously than in the prior art, even on a relatively large scale. It was necessary for this that the catalyst system is not toxic (like $BF_3$ adducts), that it is not corrosive (like $ZnCl_2$, HCl, HCOOH and $H_3PO_4$), that it suppresses as far as possible unwanted side reactions such as dehydration of isophytol to phytadienes, and that it catalyzes reaction of the costly and sensitive starting materials in high yield, even when equimolar amounts are used, since the excess starting materials can be separated from the reaction product only at great expense.

We have found that this object is achieved by using a mixture of ortho-boric acid on the one hand and certain dicarboxylic acids, such as oxalic acid or tartaric acid, or a tricarboxylic acid, such as citric acid, on the other hand, in particular a mixture of ortho-boric acid and oxalic acid, which meets the stated requirements by far the best. Catalysis of the reaction by each of the components alone is inadequate. The optimal result is made possible only by the unexpected synergistic effect.

The invention accordingly relates to an improved process for preparing dl-α-tocopherol or dl-α-tocopheryl acetate by acid-catalyzed reaction of 2,3,5-trimethylhydroquinone with phytol or isophytol in a solvent at elevated temperature, with or without subsequent esterification of the resulting tocopherol with acetic anhydride, wherein the reaction is carried out in the presence of a mixture of ortho-boric acid on the one hand and oxalic acid, tartaric acid or citric acid on the other hand.

The preparation of TMH and phytol or isophytol is known and therefore does not need to be discussed.

The process takes place particularly advantageously when oxalic acid or tartaric acid, especially oxalic acid, mixed with ortho-boric acid is used as catalyst.

Condensation of TMH with phytol or isophytol is carried out according to the invention in the presence of about 0.2–7 mol %, preferably 0.5–5 mol %, of ortho-boric acid and 0.4–14 mol %, preferably 1–10 mol %, of oxalic acid, tartaric acid or citric acid per mol of TMH. The ortho-boric acid and carboxylic acid are advantageously used in the molar ratio of about 1:2.

Solvents advantageously employed for the reaction are alkylaromatic compounds such as toluene or a xylene, or else ketones with a boiling point of about 70°–140° C. It is particularly advantageous to use aliphatic ketones such as diethyl ketone or methyl isopropyl ketone. However, higher-boiling solvents such as tetralin are also very suitable if the condensation is carried out under greatly reduced pressure.

The reaction is generally carried out at about 70°–130° C., preferably 90°–110° C.

The procedure for the reaction is generally such that phytol or isophytol is slowly added to a solution of TMH and the catalyst mixture in the solvent while refluxing and removing the water from the reaction mixture azetropically. After the reaction is complete (as determined by HPLC), workup is carried out in a conventional way. When ketones are used as solvent, the latter must be removed from the reaction and replaced by a solvent which is immiscible with water, especially a hydrocarbon, so that the crude tocopherol can be washed. When alkylaromatic compounds are used as solvent, replacement thereof is unnecessary. On the other hand, the use of alkylaromatic compounds as solvent has the disadvantage that small amounts of the catalyst sublime out of the reaction mixture.

The crude tocopherol can be washed, for example, with dilute aqueous NaOH solution, with a mixture of methanol and dilute aqueous HCl and subsequently a mixture of methanol and a dilute aqueous sodium bicarbonate solution. The resulting tocopherol can be either isolated as such or else converted with excess acetic anhydride and acid catalysis into tocopheryl acetate.

The resulting tocopheryl acetate can be purified by fractional distillation under greatly reduced pressure.

The process can be carried out either batchwise or continuously.

The process according to the invention results in dl-α-tocopherol or its acetate in very good yield and purity in a straightforward and environmentally compatible manner.

EXAMPLE 1

76 g (0.5 mol) of TM were mixed with 0.973 g (15.7 mmol) of ortho-boric acid and 2.83 g (31.4 mmol) of oxalic acid in 200 g (245.2 ml) of diethyl ketone in a 1 l flask. 160 g (0.535 mol) of isophytol were added dropwise to the reaction mixture while removing water azeotropically with an efficient condenser over the course of 3 hours (h).

After the addition of isophytol was complete, the reaction mixture was refluxed for a further 30 minutes (min) and then left to cool. The TM conversion was determined by HPLC (100% methanol, Zorbax ODS 5 µm, 4 mm×25 mm, 1 ml/min, UV detector at 220 nm) as >96%.

The resulting tocopherol solution was extracted with dilute aqueous NaOH solution to remove unreacted TMH and the catalyst and was then decolorised with an aqueous alkaline solution of sodium sulfite.

The diethyl ketone was then removed by distillation under reduced pressure, and the residue was mixed with 66 g (0.646 mol) of acetic anhydride and 1.5 ml of a solution of 1 ml of $H_2SO_4$ in 100 ml of acetic anhydride and refluxed for 1 h (with HPLC checks).

The acetic anhydride/acetic acid mixture was then removed by distillation under 20 mbar, and 224 g of pure tocopheryl acetate were obtained by distillation under reduced pressure. This corresponds to a yield of 91.7% of theory.

EXAMPLES 2 TO 4

48 g (0.16 mol) of isophytol were added dropwise to a mixture of 22.8 g (0.15 mol) of TMH, 9.4 mmol of the carboxylic acid shown in the table and 0.293 g (4.7 mmol) of ortho-boric acid in 70 ml of diethyl ketone over the course of 1.5 h while removing water azeotropically with an efficient condenser. The reaction mixture was subsequently refluxed for 2 h. About 2 ml of water were removed during the reaction.

The diethyl ketone was then removed by distillation under reduced pressure (rotary evaporator with bath at 60° C. water pump), the residue was taken up in 100 ml of heptane, and the heptane solution was washed twice with 150 ml each time of a 1:1 mixture of methanol and 1N hydrochloric acid, then once with a mixture of 150 ml of methanol and 150 ml of a 2.5% strength aqueous sodium bicarbonate solution, and finally once with 75 ml of a 1:1 mixture of methanol and water.

Crude tocopherol was obtained by removing the heptane under reduced pressure (rotary evaporator with bat at 70° C., water pump).

The crude tocopherol was acetylated with 19.2 g (0.19 mol) of acetic anhydride and a catalytic amount of sulfuric acid (142°–145° C.; 4 h) and the reaction mixture was then concentrated under reduced pressure. The crude tocopheryl acetate was purified by fractional distillation under greatly reduced pressure, and the yield was determined by gas chromatography. The yields of α-tocopheryl acetate are shown in the following table.

TABLE

| Example | Carboxylic acid | Yield of α-tocopheryl acetate [% of theory] |
| --- | --- | --- |
| 2 | Oxalic acid | 95 |
| 3 | L-(+)-Tartaric acid | 85 |
| 4 | Citric acid | 69 |

EXAMPLE 5 a) A mixture of 150 ml of toluene, 22.8 g (0.15 mol) of TMH, 0.29 g (5 mmol) of ortho-boric acid and 0.85 g (10 mmol) of oxalic acid was introduced into a 500 ml apparatus with stirrer, thermometer, dropping funnel and a water trap. 48 g (0.16 mol) of isophytol were added dropwise to this mixture over the course of 1 h while removing water azeotropically with an efficient condenser (about 100° C./650 mbar), and the reaction was continued for a further 1 h. About 2.4 ml of water were removed.

The reaction mixture was then cooled to room temperature and washed 3 times with 150 ml each time of a mixture of equal parts of methanol and 1M aqueous HCl and then twice with 150 ml each time of a 50% strength aqueous methanol solution, and was finally concentrated in a rotary evaporator (bath at 65° C./30 mbar).

Then 19.2 g (0.19 mol) of acetic anhydride and a trace of sulfuric acid were added to the resulting crude tocopherol, and the mixture was refluxed for 4 h and subsequently concentrated in a rotary evaporator (bath at 65° C./30 mbar). The resulting crude tocopheryl acetate was purified by fractional distillation under greatly reduced pressure. 65.2 g of α-tocopheryl acetate distilled at 200°–210° C./0.01 mbar and had a purity of 98% according gas chromatography (GC). This corresponds to a yield of 90% of theory.

The yields can be improved slightly by altering the workup of the reaction mixture. The following workup variant b) was carried out.

b) The process was carried out as described in a) but, after completion of the reaction with isophytol, the toluene was removed by distillation (rotary evaporator, 65° C., 30 mbar) and replaced by the same amount of n-hexane, the reaction mixture was washed as described under a), and then the n-hexane was removed by distillation under reduced pressure.

The α-tocopheryl acetate obtained by fractional distillation had a purity of 98% according to GC. Yield 92% of theory.

EXAMPLE 6

A mixture of 150 ml of tetralin, 22.8 g of TMH, 0.29 g of ortho-boric acid and 0.85 g of oxalic acid was introduced into a 500 ml apparatus with stirrer, thermometer and dropping funnel. 48 g of isophytol were added dropwise to this mixture over the course of 1 h with an efficient condenser (95°–100° C. under about 80 mbar), and then reaction was continued at this temperature for 1 h. The water of reaction was removed as vapor through a heated distillation condenser and condensed in a cooled receiver (about 2.6 g). A small amount of the catalyst was carried over during this.

The mixture was subsequently cooled to 40° C., 100 ml of heptane were added and the mixture was washed three times with 150 ml each time of a solution of equal parts of methanol and 1M aqueous hydrochloric acid and subsequently twice with 100 ml each time of 50% strength aqueous methanol solution. The organic phase was concentrated by stripping off the heptane in a rotary evaporator (bath at 65° C./about 30 mbar) and tetralin was removed by distillation (50° C./about 0.5 mbar).

19.2 g of acetic anhydride and a trace of sulfuric acid were added to the residue, and the mixture was refluxed for 4 h and then concentrated in a rotary evaporator (bath at 65° C./30 mbar, finally 5 mbar). Distillation under greatly reduced pressure provided 68.6 g of α-tocopheryl acetate and 204°–210° C./0.02 mbar, which had a purity of 92% according to GC; this corresponds to a yield of 89% of theory.

We claim:

1. A process for preparing dl-α-tocopherol or dl-α-tocopheryl acetate by acid-catalyzed reaction of 2,3,5-trimethylhydroquinone with phytol or isophytol in a solvent at elevated temperature, with or without subsequent esterification of the resulting tocopherol with acetic anhydride, wherein the reaction is carried out in the presence of a mixture of ortho-boric acid and oxalic acid, tartaric acid or citric acid.

2. A process for preparing dl-α-tocopherol or dl-α-tocopheryl acetate as claimed in claim 1, wherein the reaction is carried out in the presence of a mixture of ortho-boric acid and oxalic acid.

3. A process for preparing dl-α-tocopherol or dl-α-tocopheryl acetate as claimed in claim 1, wherein the reaction is carried out in the presence of a mixture of ortho-boric acid and tartaric acid.

4. A process for preparing dl-α-tocopherol or dl-α-tocopheryl acetate as claimed in claim 1, wherein the reaction is carried out in the presence of from 0.5 to 5 mol % of ortho-boric acid and from 1 to 10 mol % of oxalic acid, tartaric acid or citric acid per mol of trimethylhydroquinone.

* * * * *